United States Patent [19]

Kazlauskas

[11] Patent Number: 4,879,421
[45] Date of Patent: Nov. 7, 1989

[54] METHOD FOR PREPARING OPTICALLY ACTIVE BINAPHTHOL AND SPIROIBIINDANOL

[75] Inventor: Romas J. Kazlauskas, Montreal, Canada

[73] Assignee: General Electric Company, Schenectady, N.Y.

[21] Appl. No.: 232,248

[22] Filed: Aug. 15, 1988

[51] Int. Cl.$^4$ .................... C07C 39/38; C07C 39/14
[52] U.S. Cl. .................... 568/737; 568/731; 568/732; 568/734; 568/735
[58] Field of Search ............ 568/735, 734, 737, 731, 568/732

[56] References Cited

U.S. PATENT DOCUMENTS 4,171,458 10/1979 Schuster et al. .................... 568/735
4,171,459 10/1979 Schuster et al. .................... 568/735

FOREIGN PATENT DOCUMENTS 196888 12/1967 U.S.S.R. .................... 568/735
2072174 9/1981 United Kingdom .................... 568/735

Primary Examiner—Werren B. Lone
Attorney, Agent, or Firm—Mary A. Montebello; James C. Davis, Jr.; William H. Pittman

[57] ABSTRACT

A method is provided for the production of optically active (S)-(−)- and (R)-(+)-binaphthol and catalyzed asymmetric hydrolysis of corresponding racemic (R,S)-(±)-binaphthol an (R,S)(±)-spirobiindanol diesters.

14 Claims, No Drawings

METHOD FOR PREPARING OPTICALLY ACTIVE BINAPHTHOL AND SPIROIBIINDANOL

BACKGROUND OF THE INVENTION

Enantiomerically pure binaphthol has found use as important constituents of asymmetric reagents used in organic synthesis. Optically active binaphthol has been used, for example, as chiral auxiliary in the preparation of chiral catalysts for asymmetric hydrogenation; the preparation of chiral crown ethers for use as stereoselective complexing agents; and the preparation of organotitanium reagents and hydroboration catalysts. Further, such optically pure binaphthol may be useful in asymmetric synthesis of chiral polymers such as polyesters, polyphenylene oxides and polyethers. Similarly, optically active spirobiindanol has found use in the preparation of chiral polycarbonates.

The acquisition of such useful optically active compounds has relied chiefly on the resolution of racemic (R,S)-±-1,1'-bi-2-naphthol and (R,S)-±-spirobiindanol as the asymmetric synthesis of such compounds involves complex multistep synthetic routes.

For example, the (R)-(+)- and (S)-(−)-1,1'-bi-2-naphthol enantiomers have been obtained by first preparing diastereomeric cinchonine salt derivatives of phosphate esters of racemic binaphthol which salts are then separated by fractional crystallization and reduced and recrystallized to produce separated (R)-(+)- and (S)-(−)-1,1'-bi-2-naphthol.

In similar manner, the (R)-(+)- and (S)-(−)enantiomers of spirobiindane acids have been obtained, for example, by preparing diastereomeric derivatives of the racemate which are then separated by fractional crystallization, reduced and recrystallized to provide optically active isomers.

Such traditional chemical methods of enantiomeric separation, however, have presented problems in the preparation of optically active isomers on a synthetic scale as such methods are tedious and expensive. In particular, the chiral derivatizing agents used to prepare diastereomers are both expensive and difficult to reuse and the separation of diastereomeric derivatives by fractional crystallization can lead to process scale up problems, for example, in the preparation of enantiomers on a synthetic scale.

HPLC methods using columns packed with chiral stationary phase have also been used for separation of enantiomers. However, such methods are typically analytical techniques and can also be difficult and expensive to scale up and perform on a synthetic scale.

In view of that above, a definite need therefore exists for a convenient and economical method for separating the enantiomers of racemic binaphthol and spirobiidanol which can be performed on a synthetic scale.

Recently, several methods of applying enzymes to organic synthesis which overcome the aforementioned disadvantages associated with traditional chemical methodology have been used in the separation of enantiomers on a synthetic scale. For instance, methods of stereoselective hydrolysis of various ester compounds by use of an esterase to obtain optically active compounds or to create chiral compounds from prochiral compounds are known. Examples of such methods include U.S. Pat. No. 4,588,694 wherein the production of optically active (S)-(+)-3-alkyl-5-acyloxymethyl-oxazolidin-2-one derivatives via esterase catalyzed asymmetric hydrolysis of corresponding racemic esters is reported; Japanese Pat. Application No. 6224439 wherein the biochemical production of (R)-4-hydroxy-2cyclopentanone from asymmetric hydrolysis of racemic 4-hydroxy-2-cyclopentanone-organic carboxylic acid ester in the presence of an esterase; and Japanese Pat. Application No. 61092596 wherein the production of optically active indoline-2-carboxylicacid is provided by esterase catalyzed asymmetric hydrolysis of (R,S)-indoline-2carboxylic acid ester.

Other examples of optically active compounds prepared by esterase catalyzed asymmetric hydrolysis are described in U.S. Pat. No. 4,731,476 (esterase catalyzed stereoselective hydrolysis of L-Leucine ester to optically pure L-Leucine); European Pat. Application No. 243167 (description of a novel esterase useful in the economic production of optically active compounds via asymmetric hydrolysis and the creation of chiral compounds from prochiral compounds); Japanese Pat. Application No. 62205042 (treatment of racemic d,l-cyclopentanone esters with esterase to effect asymmetric hydrolysis to optically active substances); Japanese Pat. Application No. 62129238 (esterase catalyzed asymmetric hydrolysis of cyclopentanone esters to optically active cyclopentanone derivatives); Japanese Pat. Application No. 61173788 (preparation of 4-chloro-3-hydroxybutyric acid by esterase catalyzed asymmetric hydrolysis of the corresponding acid ester); Japanese Pat. Application No. 61104797 (preparation of optically active 1-(4-phenoxyphenoxy)-propane-2-ol via esterase catalyzed asymmetric hydrolysis); Japanese Pat. Application No. 59118737 (stereoselective hydrolysis of d-4-cyclopentanone esters by porcine liver esterase, bovine liver esterase, lipase and the like); and Japanese Pat. Application 57193495 (preparation of optically active furanyl carboxylic acid esters via stereoselective esterase hydrolysis). See also, Ladner, et al., 106 J. Am. Chem. Soc. 7250-1 (1984) (resolution of enantiomerically pure epoxy alcohols by asymmetric lipase catalyzed hydrolysis of epoxy alcohol esters); Findeis, et al., 19 Annu. Rep. Med. Chem. 263 (1984) (enantiospecific hydrolysis of racemic threo esters with pig liver esterase to the (−)-acid); and Iriuchijma, et al., 46 Agric. Biol. Chem. 1907 (1982) (resolution of racemic imidazolone to (+)-biotin via stereoselective esterase hydrolysis). For further examples, see Laumen, et al., 26 Tetrahedron Lett. 407–410 (1985); Schneider, et al., 23 Angew. Chem. Int. Ed. Engl. 64–66 (1984); and Wang, et al., 106 J. Am. Chem. Soc. 3695 (1984).

In view of the above, it is therefore an object of the present invention to provide a novel and simple method for preparing optically active binaphthol and spirobiindanol from respective racemates on a synthetic scale. It is a further object of this invention to provide such a method wherein said optically active compounds are conveniently prepared from the enzyme catalyzed stereoselective hydrolysis of corresponding racemic esters.

SUMMARY OF THE INVENTION

As a result of various studies, it has now been unexpectedly found that optically pure (S)-(−) and (R)-(+)-1,1'-bi-2-naphthol (binaphthol) and (S)-(−) and (R)-(+)-2,2',3,3'-tetrahydro-3,3,3',3'-tetramethyl-1,1'-spirobi-[1H-indene]-6,6'-diol(spirobiindanol) can be conveniently prepared in high enantiomeric purity on a synthetic scale by esterase catalyzed asymmetric hydrolysis of racemic corresponding esters.

In accordance with the present invention, a method is therefore provided which comprises contacting a racemic compound of (R,S)-(±)-1,1'-bi-2-naphtholorganic carboxylic acid diester or (R,S)-(±)-spirobiindanol-organic carboxylic acid diester, having the following respective formulas, [(R,S)-(±)-binaphthol(OCOR)₂-] and [(R,S)-(±)-spirobiindanol-(OCOR)2]

[(R,S)-(±)-binaphthol-(OCOR)₂]

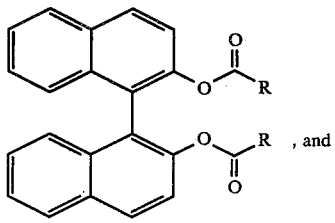

, and

[(R,S)-(±)-spirobiindanol-(OCOR)₂]

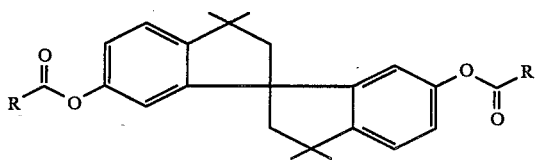

wherein R represents an alkyl, alkenyl, aryl or a 6 membered heterocyclic group having an oxygen atom or nitrogen atom as a hetero atom, or R'CO—, R'SO₂—, or R'NHCO— groups wherein R' represents an alkyl, alkenyl, aryl or a heterocyclic group, with an effective amount of enzyme having stereoselective esterase activity capable of asymmetrically hydrolyzing said compounds to optically active (S)-(—)-binaphthol and (R)-(±)-spirobiindanol, respectively, and wherein (R)-(+)-binaphthol-organic carboxylic acid diester and (S)-(—)-spirobiindanol-organic carboxylic acid diester remain substantially unaffected and can easily be converted to optically active (R)-(+)binaphthol and (S)-(+)-spirobiindanol, respectively, by routine chemical hydrolysis.

The present invention will be more fully illustrated by the following detailed description and discussion of specific embodiments.

DETAILED DESCRIPTION OF THE INVENTION

Racemic (R,S)-(±)-binaphthol-carboxylic acid diesters of formula (R,S)-(±)-binaphthol-(OCOR)₂ can be prepared by any known method including esterification of (R,S)-(±)-binaphthol by conventional chemical methods. For example, diesters of formula (R,S)-(+)-binaphthol(OCOR)₂ can be conveniently prepared by reaction of (R,S)-(±)-binaphthol with triethylamine and an appropriate acid chloride or anhydride in a suitable solvent such as ethyl ether.

The compound (R,S)-(±)-binaphthol can be obtained from any convenient source or prepared by known methods, such as described, for example, in U.S. Pat. No. 4,385,111.

In similar manner, racemic (R,S)-(±)-spirobiindanol carboxylic acid diesters of formula (R,S)-(±)-spirobiindanol-(OCOR)₂ can be prepared by any known method, for example, such as esterification of (R,S)-(±)-spirobiindanol by methods described above.

Racemic (R,S)-(±)-spirobiindanol can also be obtained from any convenient source or prepared by known methods such as described in U.S. Pat. No. 4,605,789.

The substituent group defined as R in the representative formulas (R,S)-(±)-binaphthol-(OCOR)₂ and (R,S)-(±)-spirobiindanol-(OCOR)₂ can be a lower alkyl group, for example, methyl, ethyl, propyl, isopropyl, butyl, isobutyl, hexyl, n-octyl, tert-octyl and the like; or an alkenyl group, for example, allyl, octenyl or oleyl; an aryl group, for example, phenyl or naphthyl; or a 5 or 6 membered heterocyclic group having an oxygen atom or nitrogen atom as a hetero atom, such as tetrahydropyranyl or pyrimidyl; R can also be R'CO—, R'SO₂—or R'NHCO— groups wherein R' represents an alkyl group such as methyl, ethyl, n-propyl, n-butyl, n-octyl, tert-octyl, or benzyl; an alkenyl group such as allyl, octenyl or oleyl; an aryl group such as phenyl, methoxyphenyl or naphthyl; or a heterocyclic group such as pyrimidyl or pyridyl.

For purposes of the present invention, R preferably represents a lower alkyl group having 1–7 carbon atoms, most preferably a n-pentyl or n-hexyl group.

The preparation of diesters as represented by formulas (R,S)-(±)-binaphthol-(OCOR)₂ and (R,S)-(±)-spirobiindanol-(OCOR)₂ as opposed to monoesters are preferred in the present invention. It is believed, without intending to limit the scope hereof, that the high enantiospecific hydrolysis of the aforesaid diesters provided by this invention is due in part to the requirement that two ester groups must be subsequently hydrolyzed in order to stereoselectively convert a starting diester enantiomer to the corresponding optically active diol. Thus, in the esterase catalyzed asymmetric hydrolysis of the (S)-(—)-binaphthol-(OCOR)₂ diester portion of the racemate in accordance with this invention, the enzyme having stereoselective esterase activity selects for the (S)-(—)-binaphthol enantiomer in both hydrolysis reactions. Similarly, in the esterase catalyzed asymmetric hydrolysis of the (R)-(+)-spirobiindanol-(OCOR)₂ diesters, the esterase enzyme selects for the (R)-(+)-spirobiindanol enantiomer in both hydrolysis reactions.

In contrast, when a small amount of the (R)-(+)-binaphthol-(OCOR)₂ and (S)-(—)-spirobiindanol-(OCOR)₂ diesters are hydrolyzed in the presence of the esterase to the corresponding monoesters, it is believed that the subsequent hydrolysis to the (R)-(+)-binaphthol and (S)-(—)-spirobiindanol enantiomers is slow in comparison to the stereoselectly hydrolyzed enantiomers above.

The term "esterase" as used herein is rather nonspecific and covers a broad range of enzymes including lipases and proteinases. For purposes of the present invention, however, enzymes capable of asymmetrically hydrolyzing the (R,S)-(±)-binaphthol(OCOR)₂ and (R,S)-(±)-spirobiindanol-(OCOR)₂ diesters to optically active (S)-(—)-binaphthol and (R)-(+)-spirobiindanol, respectively, are preferably esterases capable of catalyzing the hydrolysis of carboxylic acid esters (carboxylic ester hydrolases and arylester hydrolases). Pancreatic cholesterol esterase is preferred for use in the present invention because of its high stereoselectivity in catalyzing the asymmetric hydrolysis of the aforesaid diesters to optically active (S)-(—)-binaphthol and (R)-(+)-spirobiindanol.

Cholesterol esterase enzyme suitable for use in the present invention can be obtained from any convenient source. Highly purified enzyme preparations are not critical to this invention since contaminating enzymes are probably inert to or otherwise have little or no effect on the reactants and products present in the reaction mixture. It is to be noted, however, that if an enzyme to be used herein has intrinsically low specific activity (units of catalytic activity per weight of protein), crude preparations thereof can cause practical problems by requiring unnecessarily large volumes of reaction mixtures and correspondingly large reactor volumes.

Accordingly, crude acetone powders from bovine pancreas containing cholesterol esterase are suitable for enantiospecific hydrolysis in this invention without further purification. Such crude samples display enantioselectivity similar to purified cholesterol esterase, although with a lower specific activity, and are preferred herein as such crude acetone powders are an inexpensive source of cholesterol esterase.

Protein purity can be conveniently established by conventional methods, for example, by SDS-polyacrylamide gel electrophoresis and gel filtration. In general, the purest sample of cholesterol esterase which contains less than 10% impurity proteins shows the highest specific activity. Thus samples of enzymes displaying greater activity toward substrates also contain more cholesterol esterase as shown by a protein band migrating at approximately 59,000 daltons on SDS-polyacrylamide gel electrophoresis. Electrophoresis of impure samples of cholesterol esterase show additional proteins at 43,000, 26,000 and 15,000 daltons.

The diesters to be hydrolyzed herein are substantially water insoluble and thus can be dissolved in a suitable organic solvent, preferably ethyl ether due to its ease of dissolution and subsequent simplicity of workup, prior to contact with an aqueous solution of cholesterol esterase to form an emulsified reaction mixture wherein the asymmetric hydrolysis is effected.

In a preferred embodiment of this invention, sodium taurocholate, a bile salt known to enhance the activity of pancreatic cholesterol esterase can be used in conjunction therewith in the enantiospecific hydrolysis of the (R,S)-($\pm$)-binaphthol-(OCOR)$_2$ and (R,S)-($\pm$)-spirobiindanol-(OCOR)$_2$ diesters. It is believed, without intending to limit the scope of this invention, that taurocholate may aid in the formation of an emulsion which may therefore increase the availability of diester substrate to the esterase. The sodium taurocholate salt can be conveniently dissolved in an aqueous phase to which the cholesterol esterase has been previously dissolved in, said taurocholate salt being useful in this invention in amounts ranging from about 0.01 to about 5.0 weight percent based on the dry weight of enzyme.

The concentration of the (R,S)-($\pm$)-binaphthol-(OCOR)$_2$ and (R,S)-($\pm$)-spirobiindanol-(OCOR)$_2$ diester substrates to be asymmetrical hydrolyzed in the process of this invention is not critical. In preferred embodiments, the concentration of such substrates can vary from about 0.01 to about 10 weight percent and from about 0.01 to about 10 weight percent, respectively, based on the total weight of the reaction mixture.

Similarly, the concentration of esterase required to effect asymmetric hyrolysis of the aforesaid respective diester substrates is not critical to the practice of this invention. However, in preferred embodiments, enzyme concentration will be an amount which is effective to achieve hydrolyses in a reasonable period of time and may depend on the purity of the enzyme.

The pH of the reaction medium is also not critical to the process of this invention, and may vary from about 6 to about 8.

The progress of esterase catalyzed asymmetric hydrolysis of the (R,S)-($\pm$)-binaphthol-(OCOR)$_2$ or (R,S)-($\pm$)-spirobiindanol-(OCOR)$_2$ esters to the respective optically active diols, (S)-($-$)-binaphthol and (R)-(+)-spirobiindanol, can be conveniently monitored by periodic HPLC analysis of the reaction mixture until no further reaction is indicated. The optically active (S)-($-$)-binaphthol and (R)-(+)-spirobiinadanol thus produced can be separated from the reaction mixture by crystallization.

The substantially unreacted (R)-(+)-binaphthol-(OCOR)$_2$ and (S)-($-$)-spirobiindanol-(OCOR)$_2$ diesters can then be hydrolyzed by methods well known in the art. For example, said unreacted esters can be hydrolyzed by refluxing in water, or dilute aqueous acids or by treatment with ammonia or dilute aqueous sodium or potassium hydroxide solution at elevated temperatures.

It is preferable, however, that hydrolysis of said unreacted esters be accomplished with water or ammonia to yield solutions of optically active (R)-(+)-binaphthol or (S)-($-$)-spirobiindanol which are free from salts, thus allowing increased quantitative recovery of said enantiomers.

The present invention is more particularly described and explained by means of the following detailed Examples of preferred embodiments. It is to be understood, however, that such Examples are for illustration purposes only and are not intended to limit the scope of this invention.

Substrate diesters of (R,S)-($\pm$)-1,1'-bi-2naphthol illustrated by the formula (R,S)-(+)-binaphthol-(OCOR)$_2$ are prepared in the following preferred procedure in accordance with Example 1.

EXAMPLE I

Preparation of (R,S)-($\pm$)-binaphthol-(OCOR)$_2$ Diesters

Racemic (R,S)-($\pm$)-1,1'-bi-2-naphthol is reacted with triethylamine and a stoichiometric amount of an acid chloride or acid anhydride in ethyl ether. When analysis by thin layer chromatography (silica gel eluted with 20 volume % ethyl acetate in cyclohexane and visualized by UV) shows that the diesterification reaction is complete, the reaction mixture is washed twice with a 1 molar aqueous solution of potassium bicarbonate, followed by washing with water and drying over magnesium sulfate. The following diesters are then crystallized from ethyl ether:

|  | m.p. °C. | Analysis Calculated for C$_{24}$H$_{182}$O$_4$ | Found |
|---|---|---|---|
| biacetyl | 104–7 | C 77.82 | C 77.60 |
|  |  | H 4.90 | H 5.05 |
| bispropionyl | 101.5–103.5 | C$_{26}$H$_{22}$O$_4$ |  |
|  |  | C 78.37 | C 78.07 |
|  |  | H 5.56 | H 5.77 |
| bispentanoyl | 55–60 | C$_{30}$H$_{30}$O$_4$ |  |
|  |  | C 79.27 | C 79.22 |
|  |  | H 6.65 | H 6.78 |

Bisbutanoyl, bishexanoyl, bisheptanoyl and bisoctanoyl diesters prepared as illustrated above are oils which can be purified by chromatography on silica gel eluting with petroleum ether/ethyl acetate (4:1), and further characterized by $^1$H and $^{13}$C-NMR.

Substrate diesters of (R,S)-(±)-2,2', 3,3'-tetrahydro-3,3,3',3'-tetramethyl-1,1'-spirobi[1H-indene]-6,6'-diol illustrated by the formula (R,S)-(±)-spirobiindanol-(OCOR)$_2$ are similarly prepared in the following detailed procedure as set forth in Example II.

EXAMPLE II

Preparation of (R,S)-(±)-Spirobiindanol-(OCOR)$_2$ Diesters

An appropriate acid chloride (50 millimole) is added dropwise to a solution of racemic (R,S)-(±)-2,2',3,3'-tetrahydro-3,3,3',3'-tetramethyl-1,1'-spirobi[1H-indene]-6,6'-diol (SBI-diol) (6.1 grams, 20 millimole) and triethylamine (7 millimeters, 50 millimole) in ethyl ether (100 milliliters). The resulting suspension is stirred for 1 hour after the addition of the acid chloride is complete. Analysis by TLC (silica gel eluted with 20 vol % ethyl acetate in cyclohexane and visualized by UV) indicates when the diesterification is complete. The diester is then isolated by washing the reaction mixture twice with an equal volume of 1M KHCO$_3$, twice with distilled water, followed by drying over magnesium sulfate and filtering. The solution is next concentrated by rotary evaporation to a white solid. The white solid is then recrystallized from ether-petroleum ether (acetyl through pentonoyl esters) or petroleum ether (hexanoyl through decanoyl esters) which is characterized by $^1$H- and $^{13}$C-NMR spectroscopy.

The cholesterol esterase catalyzed enantiospecific hydrolysis of substrate (R,S)-(±)-binaphthol(OCOR)$_2$ diesters to optically active (S)-(−)-1,1'-bi-2-naphthol is illustrated by the following preferred embodiment set forth below in Example III.

EXAMPLE III

Cholesterol Esterase Catalyzed Enantiospecific Hydrolysis of (R,S)-(±)-Binaphthol-(OCOR)$_2$ Diesters to Optically Active (S)-(−)-Binaphthol A bispentanoyl diester is prepared by the reaction of racemic (R,S)-(±)-1,1'-bi-2-naphthol (200 grams, 0.70 mols) with triethylamine (214 milliliters, 1.54 mols) and valeric anhydride (304 milliliters, 1.54 mols) in ethyl ether (1 liter) at room temperature for five days. The reaction solution is then washed twice with aqueous potassium bicarbonate (1 liter, 1 molar), followed by aqueous washing and drying over magnesium sulfate. The solution is then added to a mixture containing 1 liter potassium phosphate buffer (0.1 molar, PH 7.0) crude sodium taurocholate from ox bile (12 grams) and 3 liters of ethyl ether. Bovine pancreas acetone powder comprising cholesterol esterase (100 grams) is next added to the mixture in order to hydrolyze one enantiomer of the prepared diester, which mixture is then stirred to form an emulsion. The pH of the mixture is maintained at 7.1±0.3 by the addition of aqueous sodium hydroxide (1 molar). Approximately 200 milliliters of the base is added in the first 30 minutes of the ensuing hydrolysis reaction to neutralize valeric acid formed upon cholesterol esterase catalyzed hydrolysis of the residual valeric anhydride. An additional 500 milliliters of the base is then added over a period of three days. Analysis by HPLC of the reaction mixture at this point shows 38% of the diester hydrolyzed to binaphthol, 8% to monoester and 54% remaining as diester. Stirring for two days shows no additional reaction. The emulsion is then allowed to settle, the aqueous phase discarded and any remaining emulsion in the ether phase broken by the addition of magnesium sulfate. The ether phase, combined with washings, is then dried over magnesium sulfate, filtered and concentrated by evaporation. White crystals of (S)-(−)-1,1'-bi-2-naphthol which separate are collected by filtration and washed with toluene to provide a yield of 63 grams (63% of theoretical). The filtrate is then concentrated and upon the addition of hexane, (R)-(+)-1,1'-bi-2-naphthol bispentanoate crystallizes and is collected and washed with hexane for a yield of 65 grams (41% of theoretical).

Enantiomeric purity of isolated (S)-(−)-1,1'-bi-2-naphthol and (R)-(+)-1,1'-bi-2-naphthol bispentanoate is established by separation of enantiomers on a chiral HPLC column containing ionically bonded chiral N-(3,5-dinitrobenzoyl) phenylglycine. The (S)-(−)-1,1'-bi-2-naphthol is found to be in very high enantiomieric purity (99.9% ee) and the (R)-(+)-1,1'-bi-2-naphthol bispentanoate with lower purity (96% ee).

The enantiospecific hydrolysis describes above can further be illustrated by the following scheme:

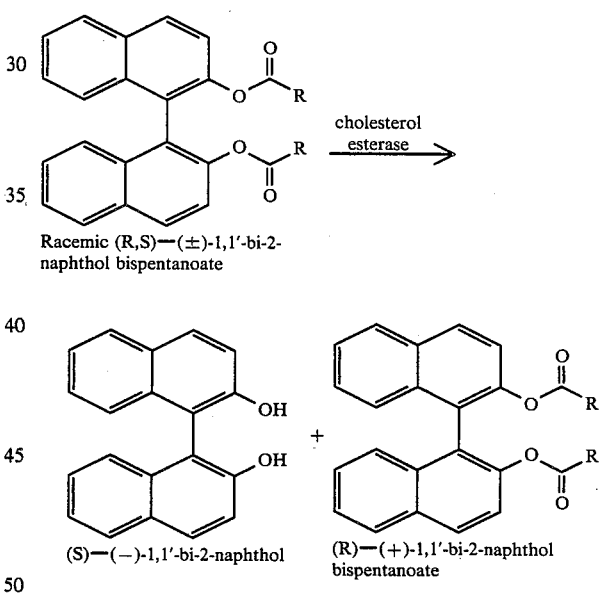

In similar manner as Example 2 commercial samples of cholesterol esterase are shown to catalyze the enantiospecific hydrolysis of diesters of 1,1'-bi-2-naphthol listed in the following Table.

| Ester | Relative Rate[a] | % ee[b] |
|---|---|---|
| acetate | 1.0 | — |

| Ester | | Relative Rate[a] | % ee[b] |
|---|---|---|---|
| ![binaphthol structure] | acetate | 1.1 | >95% ee (S) |
| | propionate | 1.1 | >95% ee (S) |
| | Butyrate | 0.5 | >95% ee (S) |
| | pentanoate | 1.1 | >95% ee (S) |
| | hexanoate | 0.5 | >95% ee (S) |
| | Heptanoate | 0.3 | >95% ee (S) |
| | octanoate | 0.4 | >95% ee (S) |

[a] The relative rate of hydrolysis is measured using a pH stat which measures the amount of base (0.1 N NaOH) required to maintain the pH at 7.0 for an emulsion of ester (1.0 mmol) dissolved in ethyl ether (10 milliliter) and aqueous buffer (10 milliliters of 10 mM phosphate, pH 7.0, containing 30 milligrams sodium taurocholate).

[b] Enantiomeric purity of binaphthols is determined by separating the enantiomers on an HPLC column containing ionically bonded chiral N—(3,5-dinitro-benzoyl)-phenylglycine.

The esterase catalyzed asymmetric hydrolysis of (R,S)-(±)-spirobiindanol-(OCOR)$_2$ esters to optically pure (R)-(+)-spirobiindanol is illustrated by the following preferred method set forth below in Example IV.

EXAMPLE IV

Cholesterol Esterase Catalyzed Enantiospecific Hydrolysis of (R,S)-(±)-spirobiindanol-(OCOR)$_2$ Diesters

Cholesterol esterase obtained in solid form from Genzyme Corporation (10.0 grams containing 8.3 grams of protein) is added to a flask containing racemic (R,S)-(±)-spirobiindanol-dihexanoyl (333 grams, 0.66 mole) ethyl ether (4 liters), sodium taurocholate monohydrate (1.8 grams) and aqueous buffer (0.60 liters of 0.1M potassium phosphate, pH 7.5). The resulting two-phase mixture is stirred at room temperature during which time the ether phase is periodically assayed by HPLC using a Water's Associates Nova Pak reverse phase C18 column which is eluted with a linear gradient of 70% to 100% acetonitrile containing 0.06% acetic acid over minutes. The second solvent is water containing 0.06% acetic acid. Eluted peaks are detected by monitoring absorbance at 254 nm. After approximately 6 days HPLC analysis shows that approximately 56% of the diester has been hydrolyzed to optically active (R)-(+)spirobiindanol having enantiomeric purity (ee) of 68%, wherein 1% is hydrolyzed to the monoester.

The reaction is then stopped by separation of the ether and aqueous phases, after which the aqueous phase which contains the cholesterol esterase is further washed once with ethyl ether and can be stored in a refrigerator for further use.

Combined ether extracts are then concentrated and washed three times with equal volumes of aqueous potassium bicarbonate (1M) and twice with equal volumes of distilled water, then dried over MgSO$_4$ and filtered. After removal of ether under a vacuum, methylene chloride is added to the residue and the resulting suspension stirred for one hour, after which a white undissolved solid is removed by filtration which is mainly racemic (R,S)-(±)-spirobiindanol (31.5 grams) with optically active (R)-(+)-spirobiindanol in 9% ee. The filtrate is chromatographed in two portions on silica gel column eluting with methylene chloride to recover non-hydrolyzed (S)-(−)-spirobiindanoldihexanoyl and ethyl ether to recover optically active (R)-(+)-spriobiindanol which is crystallized from a mixture of petroleum and ethyl ethers to provide 55.6 grams of the enantiomer in 95% ee and a smaller fraction of 3.4 grams in 23% ee.

To recover optically active (S)-(−)-spirobi-indanol, the recovered (S)-(−)-spirobiindanol-dihexanoyl diester is hydrolyzed as follows. Combined fractions containing the diester are first evaporated to dryness and redissolved in ethyl ether (500 milliliters). Ethanol (200 milliliters) and KOH (200 milliliters of a 50% weight solution) are next added and the resulting gel allowed to stand for approximately 24 hours. An additional 1 liter of ethyl ether is added and the solution neutralized to pH 7 with concentrated HCl. The two phases are separated and the ether phase washed three times with 1M KHCO$_3$ and twice with distilled water, then dried over MgSO$_4$, and optically active (S)-(−)-spirobiindanol then crystallized from a mixture of ethyl and petroleum ethers. A total of 36 grams of (S)-(−)-spirobiindanol having ee of >95% is recovered, a second portion of 30 grams of the diol is recovered having ee of 50%.

The ee of optically active (R)-(+)- and (S)-(−)-spirobiindanol diols is easily determined by the following procedure. Diastereomeric camphanic acid diesters of the diols are first prepared by the adding (1R)-(−)-camphanic acid chloride (20 micromole, 100 microliters of a 0.2M solution in CH$_2$Cl$_2$, and triethylamine (36 micromole, 5 microliters) to a respective sample of optically active diol (2 micromole, 50 microliters of a 0.04M solution). The mixture is allowed to react for 10 minutes at room temperature and then diluted with acetonitrile (1.5 milliliters). The resulting diastereomeric esters are separated by HPLC using the procedure described hereinabove, wherein eluted peaks are detected by monitoring absorbance at 254 nm. The extinction coefficients of the two diastereomers are assumed to be equal, and ee calculated according to the following equation:

$$\text{\% enantiomeric purity (ee)} = (\text{area 1} - \text{area 2})/(\text{area 1} + \text{area 2})$$

The enantiospecific hydrolysis of racemic (R,S)-(±)-spirobiindanol-dihexanoyl diester can be further illustrated by the following scheme

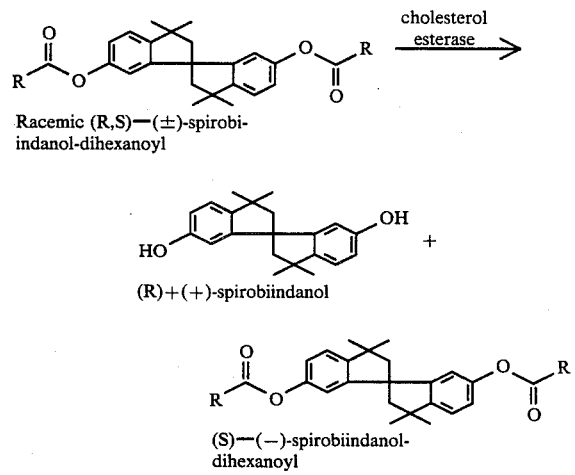

I claim:

1. A method for preparing optically active (S)-(−)-1,1'-bi-2-naphthol, comprising the steps of
   (a) reacting at a pH in the range of about 6 to about 8 an aqueous solution of pancreatic cholesterol esterase and an organic solution of an (R,S)-(+)-1,1',-bi-2-naphthol-organic carboxylic acid diester represented by the formula:

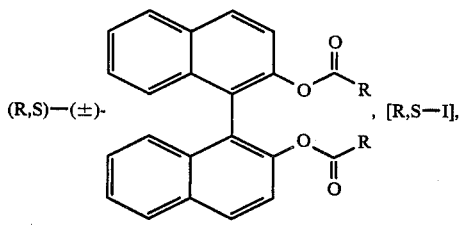, [R,S—I], the pancreatic cholesterol esterase being present in an amount, sufficient to effect asymmetric hydrolysis of (S)-(−)-1,1'-bi-2-naphthol-organic carboxylic acid diester contained in the diester of formula [R,S-I] and represented by the formula:

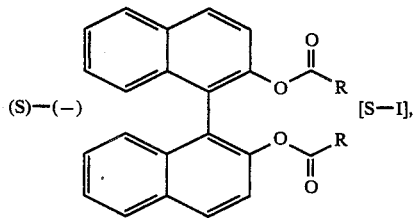 [S—I], to produce a mixture comprising (S)-(−)-1,1'-bi-2-napthanol and (R)-(+)-1,1,'-bi-2-napthanol-organic carboxylic diester, and (b) separating said binapthanol from said diester.

2. The method as defined in claim 1 wherein R is a lower alkyl group containing from 1 to 6 carbon atoms.

3. The method as defined in claim 1 wherein the cholesterol esterase is contained in acetone powders from bovine pancreas.

4. The method of claim 1, wherein R is an alkyl group containing from 1 to about 20 carbon atoms.

5. The method of claim 1, wherein R is a straight chain alkyl group containing from 1 to about 20 carbon atoms.

6. The method as defined in claim 1 further, comprising the step if hydrolyzing (R)-(+)-1,1 '-bi-2-naphthol-organic carboxylic diester represented by the formula:

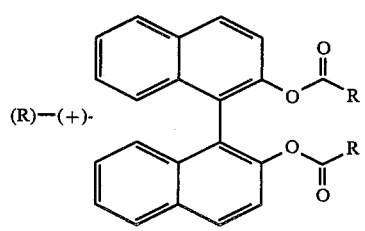

to form optically active (R)-(+)-1,1,'-bi-2-napthanol.

7. The method as defined in claim 1 wherein R is an n-hexane group.

8. A method for preparing optically active (R)-(+)-spirobiindanol comprising the step of
(a) reacting at a pH in the range of about 6 to about 8 an aqueous solution of pancreatic cholesterol esterase and an organic solution of an (R,S)-(+)-spirobiindanol-organic carboxylic acid diester represented by the formula:

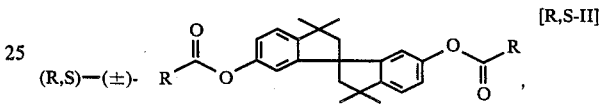, the pancreatic cholesterol esterase being present in an amount sufficient to effect asymmetric hydrolysis of (R)-(+)-spirobiindanol-organic carboxylic acid diester contained in the diester of formula [R,S-II] and represented by the formula:

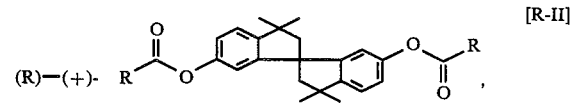, to produce a mixture comprising (R)-(+)-spirobiindanol and (S)-(−)-spirobiindanol-organic carboxylic acid diester, and (b) separating said spirobiindanol from said diester.

9. The method as defined in claim 8 further comprising the step of hydrolyzing (S)-(−)-spirobiindanolorganic carboxylic acid diester of formula [S-II]to form optically active (S)-(−)-spirobiindanol.

10. The method as defined in claim 8 wherein R is an alkyl group containing from 1 to about 20 carbon atoms.

11. The method of claim 10 wherein R is a straight chain alkyl group containing from 1 to about 20 carbon atoms.

12. The method as defined in claim 11 wherein R is a lower alkyl group containing from 1 to 6 carbon atoms.

13. The method as defined in claim 12 wherein R is an n-hexane group.

14. The method as defined in claim 8 wherein the cholesterol esterase is contained in acetone powders from bovine pancreas.

* * * * *

UNITED STATES PATENT AND TRADEMARK OFFICE
CERTIFICATE OF CORRECTION

PATENT NO. :   4,879,421

DATED      :   November 7, 1989

INVENTOR(S) :  Romas J. Kazlauskas

It is certified that error appears in the above-identified patent and that said Letters Patent is hereby corrected as shown below:

Title page, line 2 of the Abstract, after "and" insert --(S)-(-)- and (R)-(+)-spirobindanol from the esterase--.

Signed and Sealed this

Ninth Day of October, 1990

Attest:

HARRY F. MANBECK, JR.

Attesting Officer

Commissioner of Patents and Trademarks